United States Patent [19]

Wilk et al.

[11] Patent Number: 5,269,767
[45] Date of Patent: Dec. 14, 1993

[54] DEVICE AND RELATED METHOD FOR USE IN SINUS SURGERY

[76] Inventors: Peter J. Wilk, 185 West End Ave., New York, N.Y. 10023; James Z. Cinberg, 167 N. Ridgewood Rd., South Orange, N.J. 07079

[21] Appl. No.: 876,197

[22] Filed: Apr. 30, 1992

[51] Int. Cl.$^5$ .............................................. A61M 5/24
[52] U.S. Cl. ........................... 606/204.25; 606/204.15; 128/649; 128/774
[58] Field of Search ...................... 128/32, 51, 52, 645, 128/649, 650, 651, 652; 206/363, 438; 606/201, 204.15, 204.25

[56] References Cited

U.S. PATENT DOCUMENTS

| 731,543 | 6/1903 | Carpenter | 128/51 |
|---|---|---|---|
| 3,070,087 | 9/1959 | Sittel | 128/649 |
| 4,243,028 | 1/1981 | Puyana | 606/201 |
| 4,583,643 | 4/1986 | Sanderson | 206/438 |
| 5,078,728 | 1/1992 | Giarratano | 606/201 |

FOREIGN PATENT DOCUMENTS 748282  4/1956  United Kingdom ................ 128/652

Primary Examiner—C. Fred Rosenbaum
Assistant Examiner—Noelle Kent Gring
Attorney, Agent, or Firm—R. Neil Sudol; Henry D. Coleman

[57] ABSTRACT

A device for use during sinus surgery comprises a housing, a pair of straps connected to the housing for attaching the housing to a patient's head so that the housing is juxtaposed to an eyeball of the patient, and a pressurization component mounted to the housing for automatically exerting a varying pressure on the patient's eyeball. The pressure exerted is controlled to provide a regular pulsation of the eye in the event that the bony orbit between the sinus cavity and the eye is thin or perforated.

7 Claims, 1 Drawing Sheet

DEVICE AND RELATED METHOD FOR USE IN SINUS SURGERY

BACKGROUND OF THE INVENTION

This invention relates to sinus surgery. More particularly, this invention relates to a safety device for use during sinus surgery to lower the chances of injury to the eye or its ancillary organs. This invention also relates to an associated method or technique utilizable during sinus surgery to decrease the incidence of injury to the eye organs.

During sinus surgery, a nasal endoscope is inserted through a patient's nostril to enable visualization of nasal or sinus tissues. Also inserted through the same nostril is an operating instrument such as a sinus or biopsy forceps. The operating physician or surgeon controls the forceps to extract tissue particles and other matter in response to the visual image provided through the endoscope.

The bone structure underlying the eyeball and separating the eye and its surrounding fatty tissue and ancillary organs from the sinus cavity is an extremely thin and delicate structure. It is occasionally perforated during sinus surgery. Upon the perforation of the bone, the eyeball or ancillary organs such as the optic nerve, the retinal artery, or the muscles moving the eye, may be damaged. Complications vary from a mild blackeye to partial or total loss of vision.

To guard against the possibility of injuring the eye in this way, the sinus surgeon can periodically press the eyeball (globe) with a finger or thumb. If the bone separating the eye from the sinus cavity is perforated or has become very thin, the pressure on the globe produces a movement visible through the nasal endoscope. The surgeon then knows that further removal of tissue in the area of the movement is hazardous and may result in injury to the eye.

OBJECTS OF THE INVENTION

An object of the present invention is to provide a device and an associated method which facilitate the performance of sinus surgery.

Another, more particular, object of the present invention is to provide such a device and method which frees the surgeon from having to apply pressure to the eyeball.

Another object of the present invention is to provide such a device which is easy to use.

A further particular object of the present invention is to provide such a device which automatically applies a periodic pressure to a patient's eyeball during sinus surgery.

SUMMARY OF THE INVENTION

A device for use during sinus surgery comprises, in accordance with the present invention, a housing, an attachment element connected to the housing for attaching the housing to a patient's head so that the housing is juxtaposed to an eyeball of the patient, and a pressurization component mounted to the housing for automatically exerting a varying pressure on the patient's eyeball.

Pursuant to another feature of the present invention, the pressurization component includes a contact member with a concave surface adapted to apply pressure to an extended surface of the patient's globe. The contact member is shiftably mounted to the housing.

According to an additional feature of the present invention, the pressurization component further includes a drive such as an electrical motor or a solenoid operatively connected to the contact member for shifting the contact member in a reciprocating motion.

Preferably, the varying pressure on the eyeball is exerted with a regular rhythm or, more particularly, a constant rhythm or beat.

An associated method for use during sinus surgery comprises the steps of (a) providing a housing having a shiftable contact member, (b) attaching the housing to a patient's head over an eyeball of the patient, and (c) automatically shifting the contact member relative to the housing and concomitantly relative to the patient's head in a reciprocating type motion to exert a varying pressure on the patient's eyeball.

A device and an associated method in accordance with the present invention facilitate the performance of sinus surgery. The necessity of remembering to manually press the patient's eyeball and of actually diverting the surgeon's hand or hands from the operative field has been eliminated, thereby freeing one of the surgeon's hands for other activity.

A device in accordance with the present invention is easy to use and straightforward in its application.

DETAILED DESCRIPTION

Figure 1:
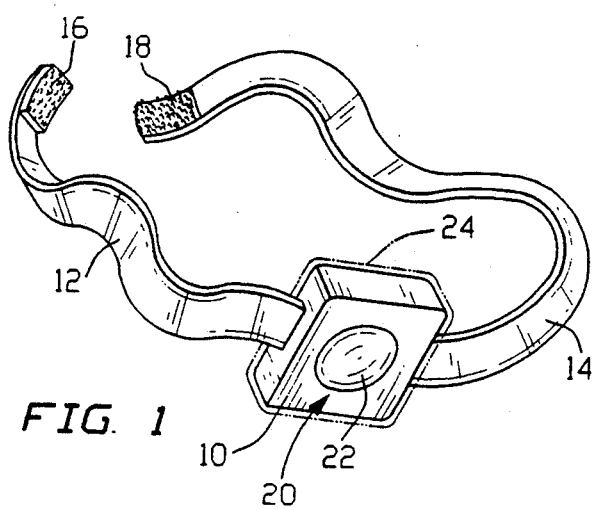
FIG. 1 is a perspective view of a device in accordance with the present invention for automatically applying a periodic pressure to an eyeball during sinus surgery.
Figure 2:
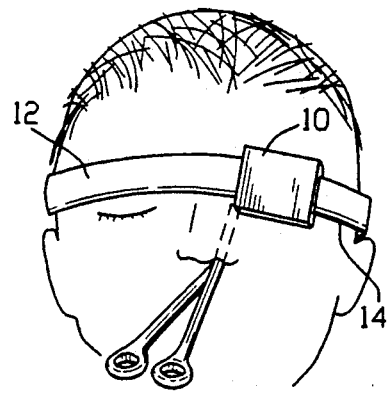
FIG. 2 is a schematic view, on a reduced scale, of the device of FIG. 1 attached to a person's head during sinus surgery.

As illustrated in FIGS. 1 and 2, a device for automatically applying a periodic pressure to the eyeball during sinus surgery comprises a housing 10 having a pair of straps 12 and 14 provided with VELCRO type hook and loop fasteners 16 and 18 for attaching the housing over a patient's eye, as shown in FIG. 2. Movably mounted to housing 10 is a contact member 20 having a concave surface 22 for engaging the eyelid of the patient so as to enable the application of pressure over an extended surface of the cornea. A disposable flexible envelope 24 removably surrounds housing 10.

Figure 3:
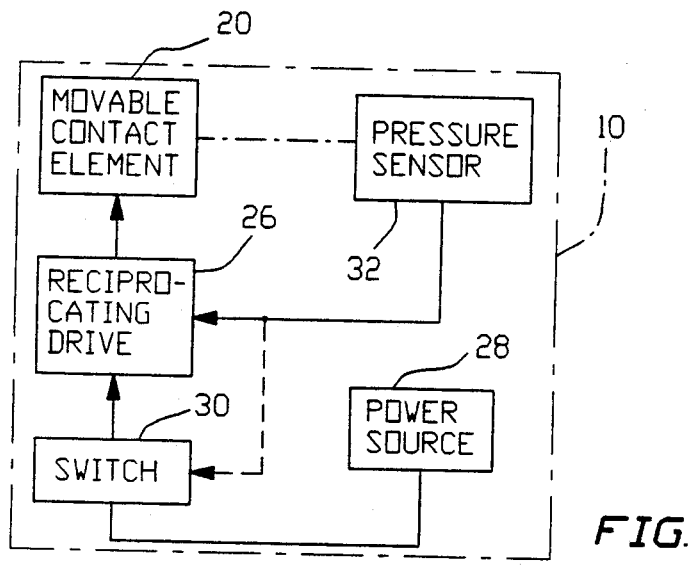
FIG. 3 is a block diagram of operative components of the eyeball pressurization device of FIGS. 1 and 2.

In order to apply periodic pressure to the eyeball, housing 10 contains a reciprocating drive component 26 operatively connected to contact member 20, as illustrated in FIG. 3. Drive 26 is energized by a power source 28 via a manually operable switch 30 mounted to housing 10. A pressure sensor 32 is provided to regulate the amount of pressure applied to the eye and to ensure that a predetermined pressure threshold is not exceeded. Pressure sensor 32 may be operatively coupled with contact member 20 to monitor eye pressure. Alternatively, pressure sensor 32 may have a separate contact with the eye to monitor the pressure therein. Sensor 32 is connected to drive 26 for either controlling the energization thereof or automatically deactivating the drive in the event that the pressure on the eye exceeds the predetermined threshold or maximum. To cut off the power, sensor 32 may be connected to switch 30 for operating that element.

In the event of a power cut off, an alarm generator (not illustrated) may issue an audible alarm signal to indicate that the pressurization device has been disabled.

Figure 4:
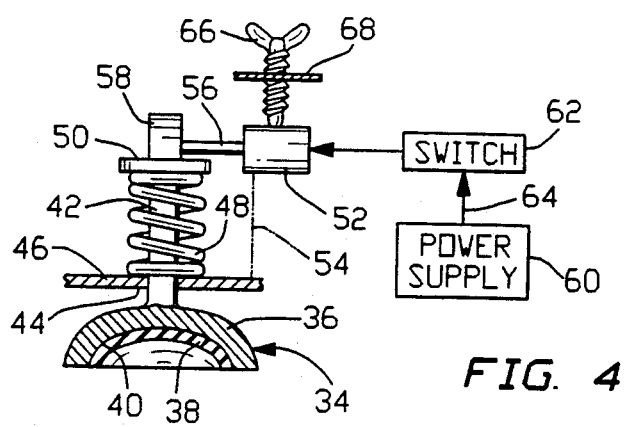
FIG. 4 is partially a cross-sectional view and partially a block diagram of a particular embodiment of an eyeball pressurization device in accordance with the present invention.

As illustrated in FIG. 4, an eye contact member 34 includes a cup-shaped portion 36 lined with a rubber pad 38. Cup-shaped portion has a concave inner surface 40 to which pad 38 conforms. Inner surface 40 and, accordingly, pad 38 have a profile which generally matches a patient's globe.

Eye contact member 34 further includes a shaft portion 42 connected to cup-shaped portion 36 and traversing an aperture 44 in a housing wall or panel 46. A compression spring 48 is disposed between wall 46 and a flange 50 at an inner end of shaft portion 42 and serves to bias eye contact member 34 towards a retracted position in which cup-shaped portion 36 is juxtaposed to wall 46.

An electric motor 52 is shiftably mounted to housing wall 46, directly or indirectly, as indicated by a dot-dash line 54. Motor 52 has a rotor shaft 56 which carries an eccentric camming element 58 which is disposed in engagement with flange 50. Rotation of rotor shaft 56 during energization of motor 52 causes, via camming element 58 and flange 50, a reciprocation of eye contact member 34 in opposition to the restoring or biasing force exerted by compression spring 48. Motor 52 is energized by a power supply 60 via a manually operable switch 62. Power supply 60 may be carried on board the housing or may be a remote source connected to motor 52 via a cord 64.

A winged set screw 66 traversing a housing panel 68 engages motor 52 for purposes of setting a maximum pressure magnitude. In addition, a pressure sensor (not shown in FIG. 4) may be included as a safety measure. The pressure sensor may be connected, for example, to flange 50 for monitoring the location thereof prior to and during the energization of motor 52. The compression of spring 48 is a measure of the applied pressure.

Upon activation of energization of an intermittent eye compressing device as described herein, nasal or sinus tissues of the patient are visually monitored via a nasal endoscope (not shown) inserted through a nostril of the patient. A surgical instrument such as a sinus or biopsy forceps (not shown) inserted through the same nostril as the endoscope is operated by a surgeon while the eyeball or globe is being periodically pressed. The surgeon can thus monitor bony tissues inside the nasal cavity to determine whether the bone separating the eye from the nasal cavity has been weakened by the surgical operations.

Although the invention has been described in terms of particular embodiments and applications, one of ordinary skill in the art, in light of this teaching, can generate additional embodiments and modifications without departing from the spirit of or exceeding the scope of the claimed invention. For instance, the eye contact member for periodically applying pressure to a globe can simply take the form of a wheel of eccentric circumference having an arc which presses the eye during a portion of a rotation and another arc which is separated from the eye during the remainder of a rotary cycle. Such a wheel is essentially camming element 58 in FIG. 4.

Other drive mechanisms for automatically applying a periodic pressure are equivalent to the drives particularly disclosed herein. Instead of an electric motor, pressure may be applied via a solenoid. Alternatively, a drive element may be formed from a shape memory substance which is subjected to varying temperature from a heater. As the drive is alternatively heated and cooled, it alternately expands and contracts to drive an eye contact member.

In an equivalent device for applying pressure to a patient's eyeball during sinus surgery, pressure is exerted pneumatically or hydraulically from a remote pressure source via a conduit extending to the patient's head. A valve operatively connected to the conduit controls the application of pressure to the eyeball. In either case, it is necessary to attach a housing or casing element to the person's head over the eyeball, with the housing containing a pressure application component. For instance, a diaphragm may form a movable wall of a pressurization chamber in the housing. The diaphragm carries or is connected to a globe contact member with a concave cornea matching surface.

Accordingly, it is to be understood that the drawings and descriptions herein are preferred by way of example to facilitate comprehension of the invention and should not be construed to limit the scope thereof.

What is claimed is:

1. A method for use during sinus surgery, comprising the steps of:
   providing a housing having a shiftable contact member;
   attaching said housing to a patient's head over an eyeball of the patient;
   automatically shifting said contact member relative to said housing and concomitantly relative to the patient's head in a reciprocating type motion to exert a varying pressure on the patient's eyeball;
   inserting a nasal endoscope through a nostril of the patient to enable visualization of nasal or sinus tissues;
   also inserting through said nostril a surgical instrument;
   operating said surgical instrument during said step of shifting; and
   visually monitoring tissues inside said nostril via said endoscope during said steps of shifting and operating.

2. The method defined in claim 1 wherein said reciprocating type motion has a regular rhythm.

3. The method defined in claim 2 wherein said reciprocating type motion has a constant rhythm.

4. The method defined in claim 1 wherein said step of automatically shifting includes the step of operating a drive element mounted to said housing.

5. The method defined in claim 1 wherein said step of attaching includes the step of engaging with said contact member a closed eyelid of the patient, pressure being exerted on t he patient's eyeball through the closed eyelid.

6. A method for use during sinus surgery, comprising the steps of:
   inserting a surgical instrument through a nostril of a patient;
   using said surgical instrument to operate an organic tissues of the patient;

automatically exerting a regularly rhythmic pressure on an eyeball of the patient during said step of using; and visually monitoring tissues inside said nostril during said step of exerting to determine whether bony tissues of the patient are inadvertently thinned by use of said surgical instrument.

7. The method defined in claim 6, further comprising the steps of:

providing a housing having a shiftable contact member; and attaching said housing to a patient's head over an eyeball of the patient, said step of exerting including the step of automatically shifting said contact member relative to said housing and concomitantly relative to the patient's head in a continuous reciprocating type motion.

* * * * *